(12) United States Patent
Bloomquist

(10) Patent No.: US 12,336,698 B2
(45) Date of Patent: *Jun. 24, 2025

(54) BIOMATERIAL OCCLUDER DELIVERY MECHANISM

(71) Applicant: St. Jude Medical, Cardiology Division, Inc., St. Paul, MN (US)

(72) Inventor: Alex Bloomquist, Hennepin County, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/545,792

(22) Filed: Dec. 19, 2023

(65) Prior Publication Data

US 2024/0115249 A1 Apr. 11, 2024

Related U.S. Application Data

(63) Continuation of application No. 17/327,269, filed on May 21, 2021, now Pat. No. 11,883,014.

(Continued)

(51) Int. Cl.
*A61B 17/00* (2006.01)
*A61B 17/12* (2006.01)

(52) U.S. Cl.
CPC ...... *A61B 17/0057* (2013.01); *A61B 17/1204* (2013.01); *A61B 2017/00606* (2013.01);

(Continued)

(58) Field of Classification Search
CPC ............ A61B 17/0057; A61B 17/1204; A61B 2017/00606; A61B 2017/00623; A61B 2017/00867

See application file for complete search history.

(56) References Cited

U.S. PATENT DOCUMENTS

| 3,874,388 A | 4/1975 | King et al. | |
| 5,904,703 A * | 5/1999 | Gilson | A61B 17/0057 606/213 |

(Continued)

FOREIGN PATENT DOCUMENTS

| WO | 9313712 A1 | 7/1993 |
| WO | 2020006026 A1 | 1/2020 |
| WO | 2020060587 A1 | 3/2020 |

OTHER PUBLICATIONS

European Extended Search Report for EP Patent Application No. 21175212.6, mailed Jan. 3, 2022, 21 pages.

*Primary Examiner* — Alexander J Orkin

(57) ABSTRACT

A medical device including a removable frame and biomaterial cover, methods of assembling and using the same, and a delivery system including the same are described herein. The medical device includes a frame having proximal and distal ends, the frame including a proximal disc at the proximal end, a distal disc at the distal end, and a connecting segment connecting the proximal and distal discs. Each of the proximal and distal discs includes a respective plurality of prongs, the plurality of prongs each extending from the connecting segment to a free end. The medical device further includes at least one biomaterial cover including an outer section and an inner section defining a cavity therebetween, wherein at least one of the proximal and distal discs of the frame is positioned in the cavity.

20 Claims, 10 Drawing Sheets

Related U.S. Application Data

(60) Provisional application No. 63/028,423, filed on May 21, 2020.

(52) U.S. Cl.
CPC ............... *A61B 2017/00623* (2013.01); *A61B 2017/00632* (2013.01); *A61B 2017/00867* (2013.01); *A61B 2017/12095* (2013.01)

(56) References Cited

U.S. PATENT DOCUMENTS

| | | | |
|---|---|---|---|
| 6,174,322 B1 * | 1/2001 | Schneidt | A61B 17/12172 606/213 |
| 6,238,416 B1 | 5/2001 | Sideris | |
| 6,355,052 B1 | 3/2002 | Neuss et al. | |
| 7,625,392 B2 * | 12/2009 | Coleman | A61B 17/08 606/151 |
| 8,795,329 B2 | 8/2014 | Forde et al. | |
| 8,888,811 B2 | 11/2014 | Levin et al. | |
| 11,883,014 B2 * | 1/2024 | Bloomquist | A61B 17/0057 |
| 2003/0139819 A1 | 7/2003 | Beer et al. | |
| 2004/0073242 A1 * | 4/2004 | Chanduszko | A61B 17/12172 606/157 |
| 2004/0143292 A1 | 7/2004 | Marino et al. | |
| 2004/0225324 A1 * | 11/2004 | Marino | A61B 17/0057 606/213 |
| 2005/0065548 A1 | 3/2005 | Marino et al. | |
| 2005/0288706 A1 | 12/2005 | Widomski et al. | |
| 2006/0009800 A1 | 1/2006 | Christianson et al. | |
| 2006/0052821 A1 * | 3/2006 | Abbott | A61B 17/064 606/213 |
| 2006/0116710 A1 * | 6/2006 | Corcoran | A61B 17/0057 606/200 |
| 2006/0122647 A1 | 6/2006 | Callaghan et al. | |
| 2006/0224183 A1 * | 10/2006 | Freudenthal | A61B 17/12031 606/213 |
| 2007/0073337 A1 * | 3/2007 | Abbott | A61B 17/0057 606/213 |
| 2007/0185529 A1 | 8/2007 | Coleman et al. | |
| 2009/0054912 A1 * | 2/2009 | Heanue | A61B 17/0644 128/898 |
| 2010/0121370 A1 | 5/2010 | Kariniemi | |
| 2011/0184439 A1 | 7/2011 | Anderson et al. | |
| 2011/0295283 A1 | 12/2011 | Darois et al. | |
| 2012/0010644 A1 | 1/2012 | Sideris et al. | |
| 2012/0071918 A1 | 3/2012 | Amin et al. | |
| 2013/0018414 A1 | 1/2013 | Widomski et al. | |
| 2015/0005809 A1 | 1/2015 | Ayres et al. | |
| 2015/0005810 A1 | 1/2015 | Center et al. | |
| 2015/0080945 A1 | 3/2015 | Michalak | |
| 2016/0249898 A1 | 9/2016 | Widmer et al. | |
| 2019/0046170 A1 | 2/2019 | Coyle et al. | |
| 2019/0200970 A1 | 7/2019 | Onushko et al. | |
| 2021/0121179 A1 | 4/2021 | Ben-David et al. | |

* cited by examiner

BIOMATERIAL OCCLUDER DELIVERY MECHANISM

CROSS-REFERENCE TO RELATED APPLICATIONS

This application claims the benefit of priority to U.S. patent application Ser. No. 17/327,269, filed May 21, 2021, which claims the benefit of priority to U.S. Provisional Patent Application No. 63/028,423, filed May 21, 2020, the entire contents and disclosure of which are hereby incorporated by reference herein.

BACKGROUND OF THE DISCLOSURE

A. Field of Disclosure

The present disclosure relates generally to medical devices that are used in the human body. In particular, the present disclosure is directed to embodiments of an occlusion device that enables removal of a device frame from the occlusion device after the occlusion device is deployed in the human body. More specifically, the present disclosure is directed to an occlusion device with a temporary device frame that promotes native tissue growth while maintaining the fundamental function and effectiveness of an occluder. The embodiments and methods disclosed herein enable the removal of the device frame and the promotion of native tissue growth by the incorporation of a biomaterial cover over at least a portion of the device frame.

B. Background

An occluder is a medical device used to treat (e.g., occlude) tissue at a target site within the human body, such as an abnormality, a vessel, an organ, an opening, a chamber, a channel, a hole, a cavity, a lumen, or the like. For example, an occluder may be used in trans-catheter secundum atrial septal defect closures. Secundum atrial septal defects are common congenital heart defects that allow blood to flow between the left and right atria of the heart, decreasing cardiac output. Occluders may be employed to block this blood flow.

At least some known occluders may be formed from shape-formed braided nitinol that is permanently implanted in the target site of the human body. Accordingly, the presence of the occluder creates a permanent foreign object within the patient. The presence of a foreign object can present adverse side effects, such as erosion of tissue around the implanted device, development of arrhythmia, and, where a patient may develop a nickel allergy, adverse allergic effects.

Accordingly, it would be desirable to reduce the presence of a permanent foreign object within the body of the patient as much as possible, while maintaining the fundamental function and effectiveness of an occluder.

SUMMARY OF THE DISCLOSURE

The present disclosure generally relates to medical devices and methods of manufacturing and use thereof, which facilitate the minimization of a permanent foreign object at a target site within a patient's body while maintaining the fundamental function and effectiveness of the medical device (e.g., an occlusion device).

In one embodiment, the present disclosure is directed to a medical device for treating a target site. The medical device includes a frame having proximal and distal ends. The frame includes a proximal disc at the proximal end, a distal disc at the distal end, and a connecting segment connecting the proximal and distal discs. Each of the proximal and distal discs includes a respective plurality of prongs, the plurality of prongs each extending from the connecting segment to a free end. The medical device also includes at least one biomaterial cover, the at least one biomaterial cover including an outer section and an inner section defining a cavity therebetween, wherein at least one of the proximal and distal discs of the frame is positioned in the cavity.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

Figure 1:
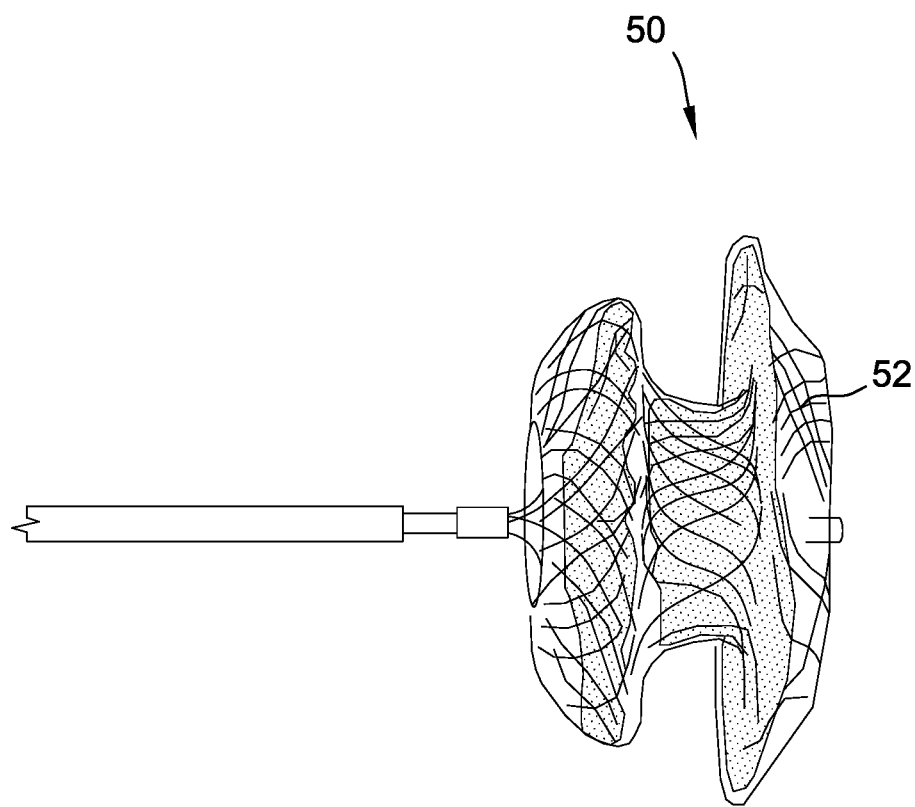
FIG. 1 illustrates a known medical device.

The present disclosure relates generally to medical devices that are used in the human body. Specifically, the present disclosure provides medical devices including occlusion devices having a biomaterial cover and a frame that is removable from the biomaterial cover, and from the patient's body, after the occlusion device has been deployed within the body at a target site. The biomaterial cover promotes tissue ingrowth such that, after a period of time, the biomaterial cover and tissue provide sufficient occlusion of the target site. Thereafter, the frame can be withdrawn from the at least one biomaterial cover without detriment to the occlusive effects of the occlusion device. In one exemplary embodiment, the frame includes a plurality of prongs, which enables de-coupling of the frame from the biomaterial cover as described herein. Accordingly, the occlusion devices of the present disclosure promote native tissue growth to achieve the fundamental function and effectiveness of the occluder, which enables the removal of the frame from the human body, to reduce or eliminate the above-described adverse effects of foreign objects within the patient's body.

The disclosed embodiments may lead to more consistent and improved patient outcomes. It is contemplated, however, that the described features and methods of the present disclosure as described herein may be incorporated into any number of systems as would be appreciated by one of ordinary skill in the art based on the disclosure herein.

It is understood that the use of the term "target site" is not meant to be limiting, as the medical device may be configured to treat any target site, such as an abnormality, a vessel, an organ, an opening, a chamber, a channel, a hole, a cavity, or the like, located anywhere in the body. The term "vascular abnormality," as used herein is not meant to be limiting, as the medical device may be configured to bridge or otherwise support a variety of vascular abnormalities. For example, the vascular abnormality could be any abnormality that affects the shape of the native lumen, such as an atrial septal defect, an LAA, a lesion, a vessel dissection, or a tumor. Embodiments of the medical device may be useful, for example, for occluding an LAA, ASD, VSD, or PDA, as noted above. Furthermore, the term "lumen" is also not meant to be limiting, as the vascular abnormality may reside in a variety of locations within the vasculature, such as a vessel, an artery, a vein, a passageway, an organ, a cavity, or the like. For ease of explanation, the examples used herein refer to the occlusion of a septal defect (e.g., an atrial septal defect or ASD).

As used herein, the term "proximal" refers to a part of the medical device or the delivery device that is closest to the operator, and the term "distal" refers to a part of the medical device or the delivery device that is farther from the operator at any given time as the medical device is being delivered through the delivery device. In addition, the terms "deployed" and "implanted" may be used interchangeably herein.

Some embodiments of the present disclosure provide an improved percutaneous catheter directed intravascular occlusion device for use in the vasculature in patients' bodies, such as blood vessels, channels, lumens, a hole through tissue, cavities, and the like, such as an atrial septal defect. Other physiologic conditions in the body occur where it is also desirous to occlude a vessel or other passageway to prevent blood flow into or therethrough. These device embodiments may be used anywhere in the vasculature where the anatomical conditions are appropriate for the design.

The medical device may include one or more discs that are at least partially covered by a biomaterial cover that acts as an occlusive material, while promoting native issue growth, which is configured to occlude or substantially preclude the flow of blood. Most commonly, blood flow may be occluded immediately. However, it is contemplated that, in some cases, some blood flow may occur. Accordingly, as used herein, "substantially preclude" or, likewise, "substantially occluded blood flow" shall mean, functionally, that minimal or trace blood flow around or through the medical device may occur for a short time, but that the body's tissue growth onto the biomaterial cover results in full occlusion after this initial time period.

The present disclosure now will be described more fully hereinafter with reference to the accompanying drawings, in which some, but not all embodiments of the disclosure are shown. Indeed, this disclosure may be embodied in many different forms and should not be construed as limited to the embodiments set forth herein; rather, these embodiments are provided so that this disclosure will satisfy applicable legal requirements. Like numbers refer to like elements throughout.

In at least some conventional or known medical devices used for the occlusion of abnormalities, such as a medical device 50 shown in FIG. 1, a metal frame 52 provides the occlusive property. The occlusive properties of these known devices arise from the facilitation of thrombosis. Metal frame 52 is formed from shape-memory material, most commonly Nitinol, that uses a single-layer, seventy-two wire braid design. As described above, when these medical devices are utilized to occlude blood flow through an abnormality, metal frame 52 becomes a permanent foreign object within the patient's body. The presence of metal frame 52 within the patient's body can potentially lead to adverse side effects such as erosion or development of a nickel allergy.

The medical devices of the present disclosure, which includes a biomaterial cover and a removable frame, minimize these disadvantages of known medical devices.

Figure 2A:
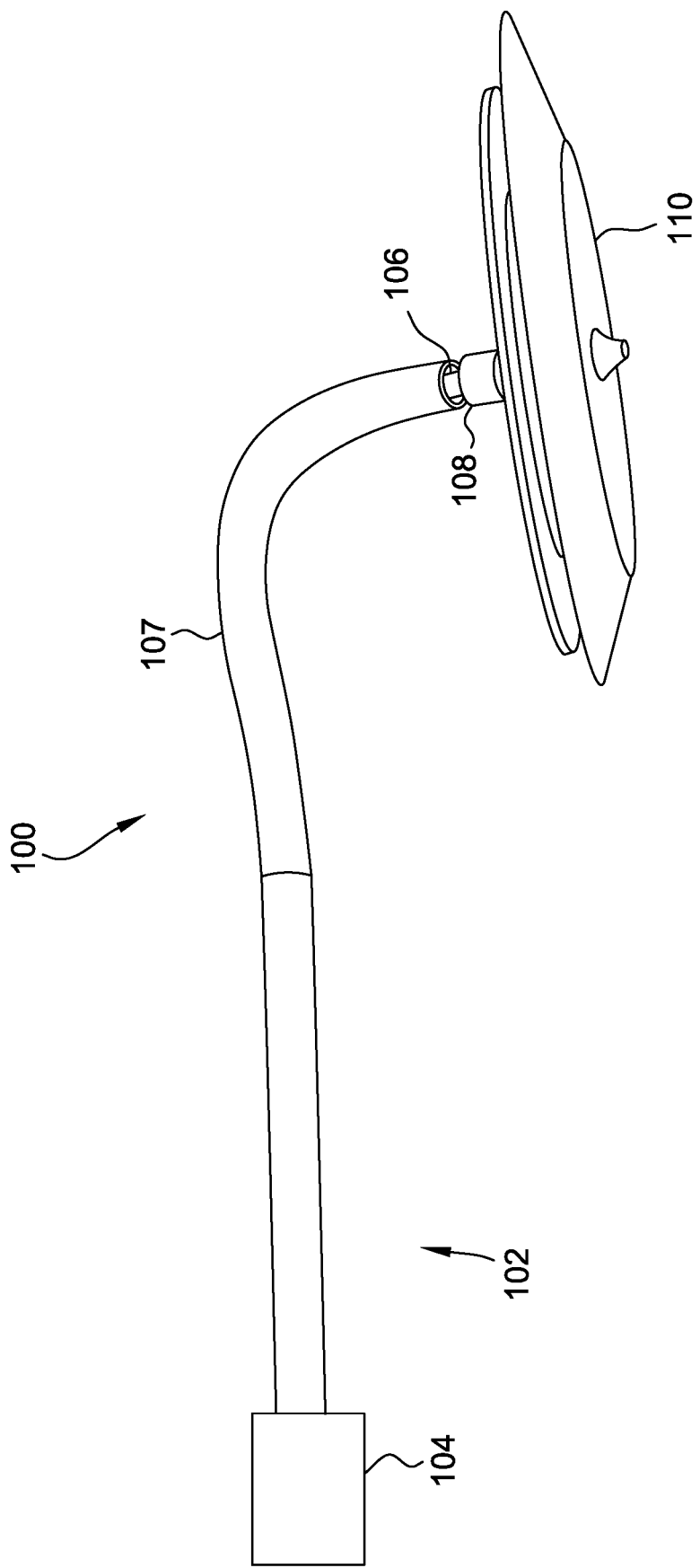
FIG. 2A is an exemplary embodiment of a delivery system including a delivery device and a medical device in accordance with the present disclosure.

Turning now to FIG. 2A, a schematic diagram of a delivery system 100 is shown. Delivery system 100 includes a delivery device 102 including a catheter 104 and a coupling member 106 configured to couple a distal end of a delivery cable 107 to a connecting member 108 of a medical device 110 for facilitating the deployment of medical device 110 at a target site. Medical device 110 is deployed to treat the target site, and, in the example embodiment, is an occlusion device ("occluder").

Figure 3:
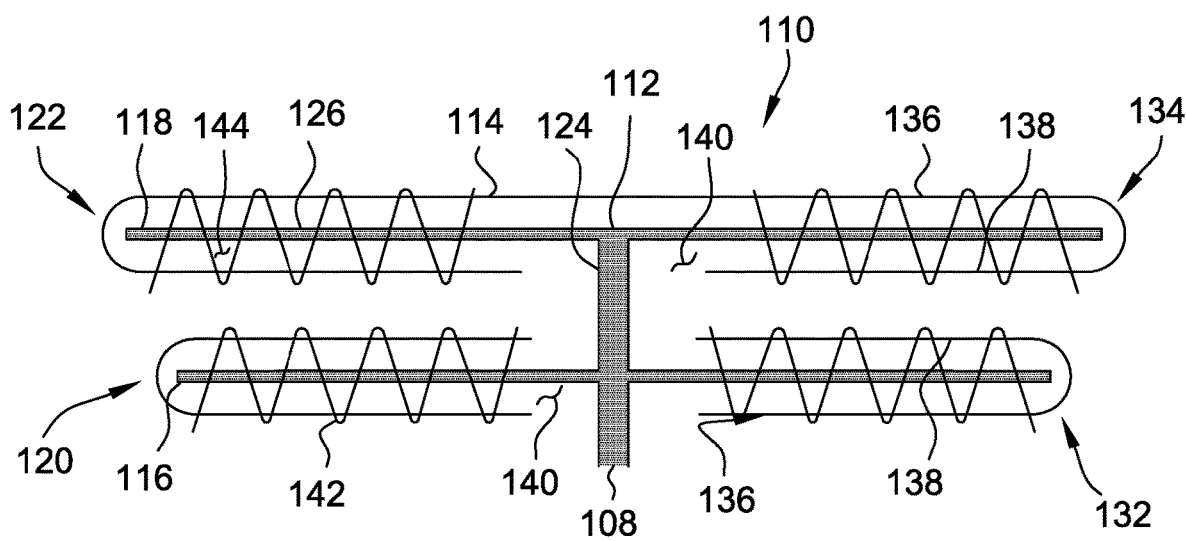
FIG. 3 illustrates a side sectional view of a first exemplary embodiment of the medical device including a frame and a biomaterial cover, in accordance with the present disclosure.
Figure 4:
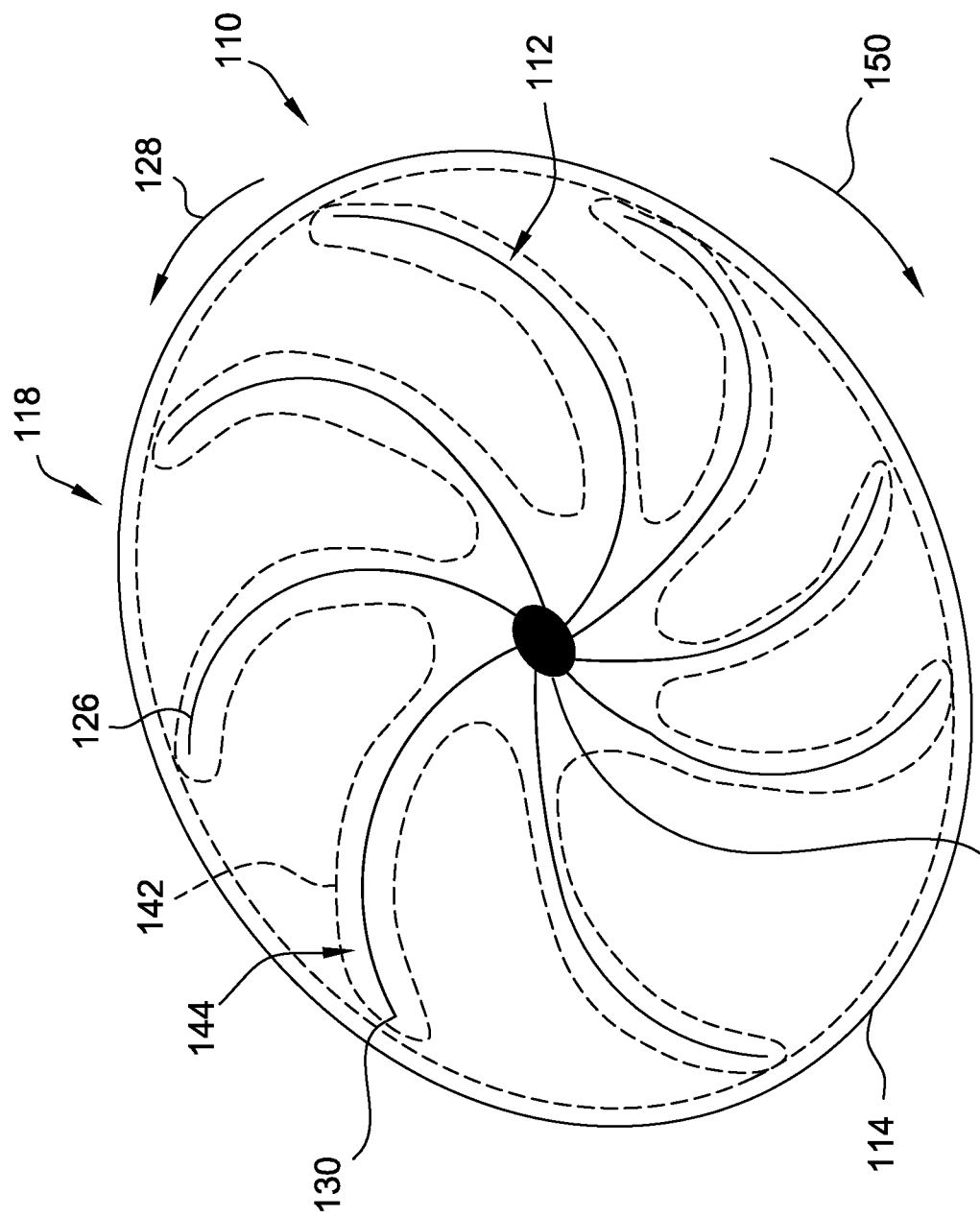
FIG. 4 illustrates a top sectional view of the medical device shown in FIG. 3.

FIGS. 3 and 4 illustrate a first exemplary embodiment of medical device 110. Specifically, FIG. 3 is a side sectional view of medical device 110, and FIG. 4 is a top sectional view of medical device 110. As shown in FIGS. 3 and 4, medical device 110 includes a device frame 112 and at least one biomaterial cover 114. Device frame 112 includes a proximal disc 116 and a distal disc 118. Proximal disc 116 at least partially defines a proximal end 120 of medical device 110 and frame 112, and distal disc 118 at least partially defines a distal end 122 of medical device 110 and frame 112.

Proximal and distal discs 116, 118 are joined together by a connecting segment 124. In the exemplary embodiment, connecting segment 124 is coaxial with proximal and distal discs 116, 118. In other embodiments, connecting segment 124 is other than coaxial with (e.g., off-center with respect to) proximal disc 116 and/or distal disc 118. In the exemplary embodiment, connecting member 108 is coupled to and extends from a proximal end of connecting segment 124. Alternatively, connecting member 108 may be coupled to and extend from proximal disc 116.

Moreover, in the exemplary embodiment, frame 112 is a unitary component, and proximal disc 116, distal disc 118, and connecting segment 124 are integrally formed with one another. Alternatively, proximal disc 116, distal disc 118, and connecting segment 124 are separately formed and are coupled together to form frame 112.

As shown in FIG. 4, distal disc 118 includes a plurality of prongs 126 that define distal disc 118. Although not shown in FIG. 4, proximal disc 116 is substantially the same as distal disc 118—that is, the description of distal disc 118 also applies to proximal disc 116.

Each of prongs 126 is arcuate in shape and extends radially outwardly in a first direction 128 that is defined from connecting segment 124 to a free end 130 of the corresponding prong 126. For example, in FIG. 4, first direction 128 is a generally counter-clockwise direction. It should be readily understood that first direction 128 may be clockwise in any other embodiment. This shape or configuration of prongs 126 is generally referred to as a "bent star" shape or configuration, referring to the overall "star" configuration of the prongs 126 within one of discs 116, 118 and the bent (e.g., curved or coiled) free ends 130 thereof. Each prong 126 is substantially similar to each other prong 126 in distal disc 118.

It is contemplated that the plurality of prongs 126 may be arranged in many different configurations. The configuration is limited only by the ability to retract the prongs from the biomaterial cover 114 to de-couple or withdraw the prongs 126 from biomaterial cover 114 and remove or withdraw frame 112 from biomaterial cover 114 (and, therefore, remove or withdraw frame 112 from medical device 110 at the target site), as described further herein.

In one embodiment, device frame 112 is formed from a shape-memory material. One particular shape memory material that may be used is Nitinol. Nitinol alloys are highly elastic and are said to be "superelastic," or "pseudoelastic." This elasticity may allow medical device 110 to be resilient and return to a preset, expanded configuration for deployment following passage in a distorted form through delivery catheter 104. Further examples of materials and manufacturing methods for medical devices with shape memory properties are provided in U.S. Publication No. 2007/0265656 titled "Multi-layer Braided Structures for Occluding Vascular Defects" and filed on Jun. 21, 2007, which is incorporated by reference herein in its entirety.

It is also understood that device frame 112 may be formed from various materials other than Nitinol that have elastic properties, such as stainless steel, trade named alloys such as Elgiloy®, or Hastalloy, Phynox®, MP35N, CoCrMo alloys, metal, polymers, or a mixture of metal(s) and polymer(s). Suitable polymers may include PET (Dacron™), polyester, polypropylene, polyethylene, HDPE, Pebax, nylon, polyurethane, silicone, PTFE, polyolefins and ePTFE. Additionally, it is contemplated that the device frame may comprise any material that has the desired elastic properties to ensure that the device may be deployed, function as an occluder, and be recaptured in a manner disclosed within this application.

Biomaterial cover 114, in the exemplary embodiment, covers or surrounds at least a portion of frame 112. For example, biomaterial cover 114 at least partially surrounds proximal disc 116 and/or distal disc 118. In the exemplary embodiment, biomaterial cover 114 defines one or more cavities in which proximal disc 116 and/or distal disc 118 are positioned. In the embodiment shown in FIG. 3, biomaterial cover 114 is two separate components, such as a first or proximal cover 132 and a second or distal cover 134. Proximal cover 132 at least partially surrounds proximal disc 116, and engages with or is coupled to frame 112 at least at proximal disc 116. Proximal cover 132 includes a first or outer section 136 and a second or inner section 138 that together define a cavity 140 in which proximal disc 116 is positioned. First section 136 and/or second section 138 engages with or is coupled to proximal disc 116. In some embodiments, second section 138 may be further removably coupled to and/or engaged with connecting segment 124 (e.g., via bioabsorbable sutures).

Distal cover 134 at least partially surrounds distal disc 118, and engages with or is coupled to frame 112 at least at distal disc 118. Distal cover 134 also includes a first section 136 and a second section 138 that also define a cavity 140. Distal disc 118 is positioned within cavity 140. First section 136 and/or second section 138 is coupled to distal disc 118. In some embodiments, second section 138 may be further removably coupled to and/or engaged with connecting segment 124 (e.g., via bioabsorbable sutures). It should be readily understood that, in some embodiments, biomaterial cover 114 includes only one of proximal cover 132 and distal cover 134.

In the exemplary embodiment, each respective first section 136 and second section 138 are coupled together and to the respective disc 116, 118 of frame 112 by bioabsorbable sutures 142. As shown in FIG. 4, bioabsorbable sutures 142 are specifically arranged to create a respective pocket 144 around each prong 126, to improve retention of prongs 126 within biomaterial cover 114. As shown in FIG. 3, these bioabsorbable sutures 142 extend through both the first and second section 136, 138 (of the respective disc) to form pockets 144. Bioabsorbable sutures 142 may also be used to couple respective first and second sections 136, 138 together. For example, bioabsorbable sutures 142 are sewn around a circumference of first and second sections 136, 138. Alternatively, where first and second sections 136, 138 are integrally formed (i.e., proximal cover 132 is a unitary component and/or distal cover 134 is a unitary component), bioabsorbable sutures 142 are not needed to couple respective first and second sections 136, 138 together. Although sutures 142 are referred to herein as bioabsorbable, it should be understood that, in some embodiments, suture 142 may not be bioabsorabable and may be formed from any suitable suture material.

Figure 5:
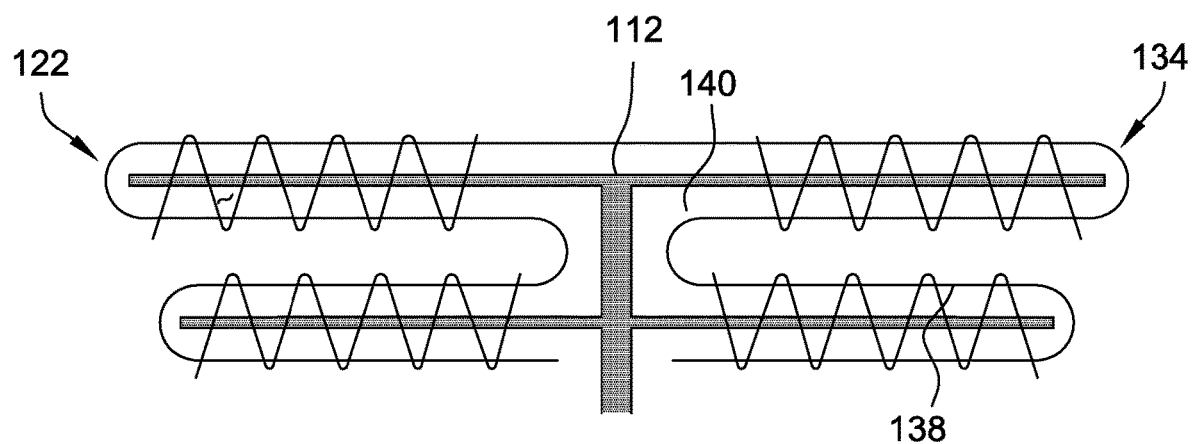
FIG. 5 illustrates a side sectional view of a second embodiment of the medical device in accordance with the present disclosure.

In some alternative embodiments, as shown in FIG. 5, biomaterial cover 114 may be a single component that substantially covers an entirety of frame 112 (e.g., both proximal and distal discs 116, 118 and connecting segment 124, but with an opening remaining at a proximal section thereof for subsequent withdrawal of frame 112). In this embodiment, biomaterial cover 114 includes a central section 146 coupled to and extending between second sections 138 of proximal and distal covers 132, 134. Biomaterial cover 114 may be a unitary component (e.g., proximal cover 132, distal cover 134, and central section 146 may be integrally formed with one another), or proximal cover 132, distal cover 134, and central section 146 may be separately formed and then coupled together to form biomaterial cover 114.

In one embodiment, biomaterial cover 114 is formed from a bioabsorbable polymer. The bioabsorbable polymer may include, for example, Poly-L-lactic acid (PLLA), Poly(glycolic acid) (PGA), Copolyesters of poly(e-caprolactone) (PCL), Trimethylene carbonate (TMC), Poly(d-diozanone) (PPDO), and combinations of various polymers. Additionally or alternatively, the biomaterial cover is formed from another polymer. The polymer may include, for example, PET (Dacron™), polyester, polypropylene, polyethylene, HDPE, Pebax, nylon, PTFE, polyolefins and ePTFE.

In other embodiments, biomaterial cover 114 may be formed from a tissue, such as pericardial tissues. The tissues may be derived from, for example, porcine, bovine, equine, and/or collagen matrices.

Figure 6:
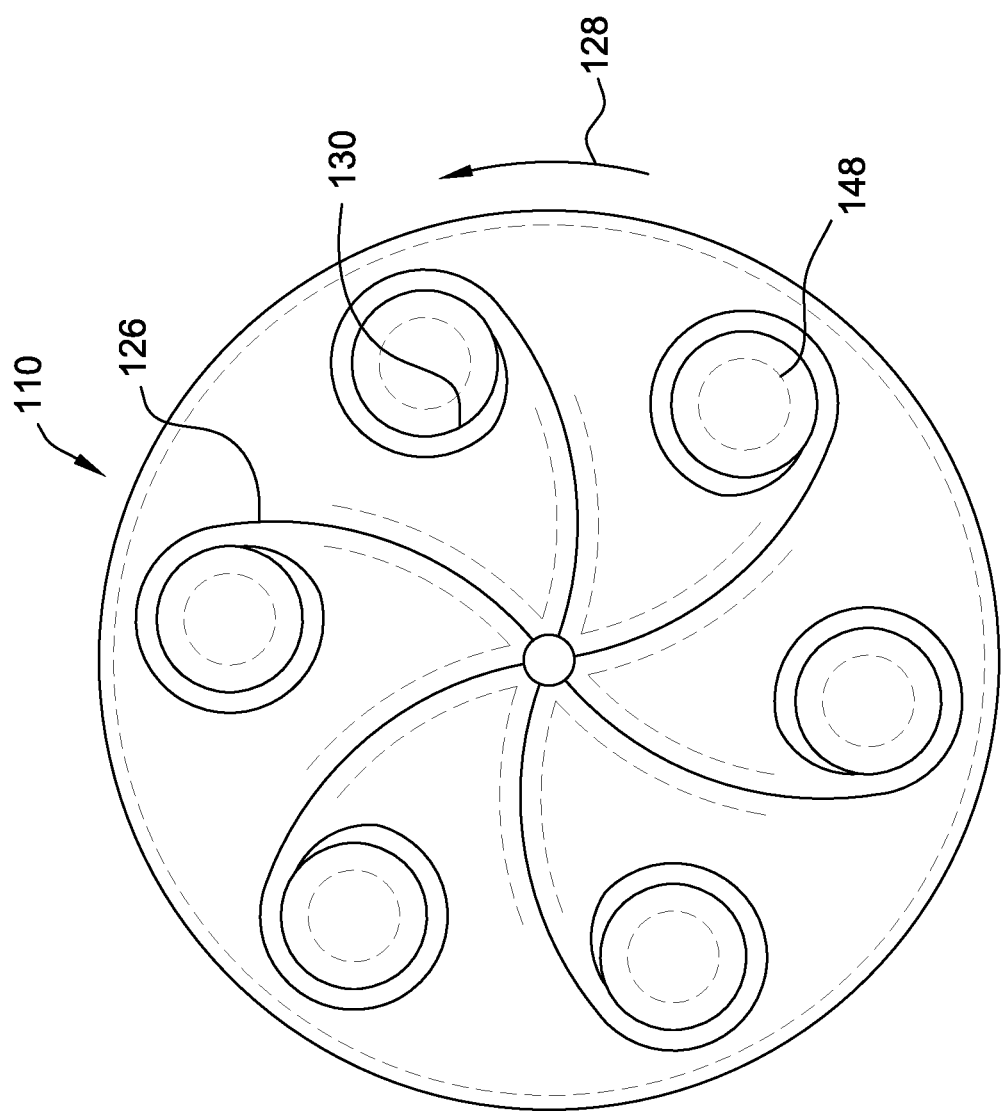
FIG. 6 illustrates a top sectional view of a third embodiment of the medical device in accordance with the present disclosure.

FIG. 6 illustrates another exemplary embodiment of medical device 110 including an alternative configuration of the plurality of prongs 126. In this embodiment, each prong 126 is arcuate and extends radially outwardly from connecting segment 124 in first direction 128, and the prong 126 also includes a helical or coiled free end 130 that completes at least one 360° rotation to further reduce the risk of free ends 130 puncturing biomaterial cover 114. Moreover, biomaterial cover 114 further includes a plurality of circular sewn pockets 148. Each coiled free end 130 of a prong 126 extends about a respective circular pocket 148. The 360° rotation about the respective circular pocket 148 may improve retention of the prong 126 within biomaterial cover 114, while still allowing for de-coupling and retraction of the prong 126 from biomaterial cover 114.

In the exemplary embodiment, to form medical device 110, proximal disc 116 and/or distal disc 118 is enclosed by a first section 136 and a second section 138 of biomaterial cover 114. Bioabsorbable sutures 142 are then applied through first section(s) 136 and second section(s) 138 to form pockets 144 that secure prongs 126 inside biomaterial cover 114.

Figure 2B:
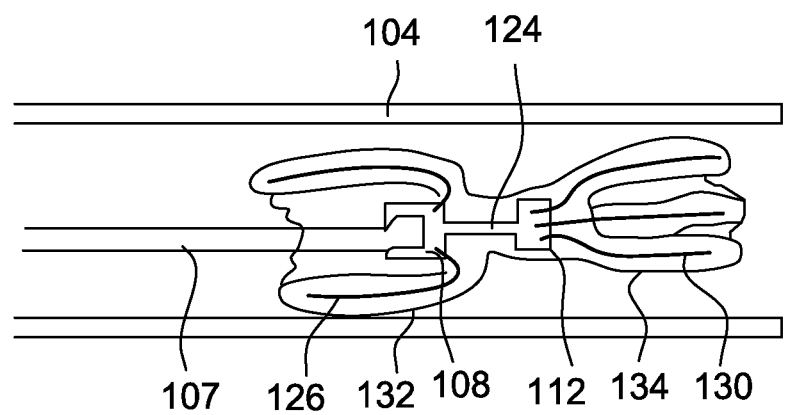
FIGS. 2B and 2C illustrate delivery of the medical device using the delivery system shown in FIG. 2A.
Figure 2C:
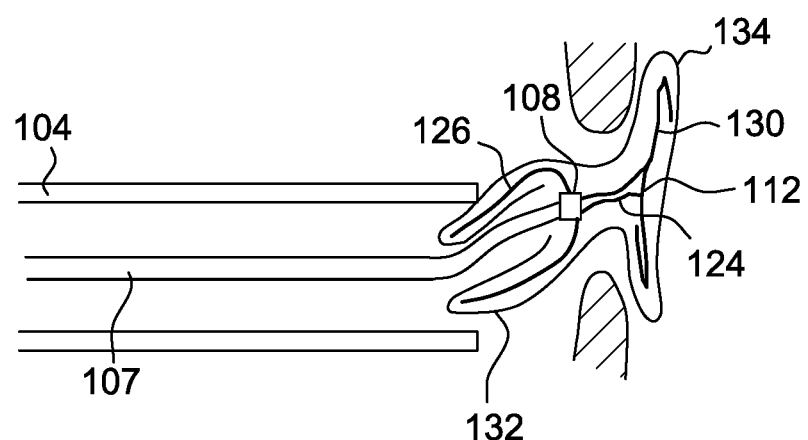

In operation, as shown in FIG. 2B, medical device 110 is advanced towards the target site within catheter 104 of delivery device 102. Proximal and distal discs 116, 118 are folded or compressed within catheter 104 during delivery. Once the target site has been reached, medical device 110 is deployed from catheter 104 into the abnormality to be occluded using delivery cable 107, as shown in FIG. 2C. Specifically, catheter 104 is positioned within or adjacent to the target site, and medical device 110 is distally advanced until distal disc 118 is released from catheter 104. As described elsewhere herein, the shape memory and/or elastic material defining frame 112 causes distal disc 118 to unfold or expand to its expanded form, on a distal side of the target site. Thereafter, catheter 104 is retracted proximally to release connecting segment 124 and proximal disc 116 from catheter 104. Proximal disc 116 unfolds or expands to its expanded form, on a proximal side of the target site.

Figure 9:
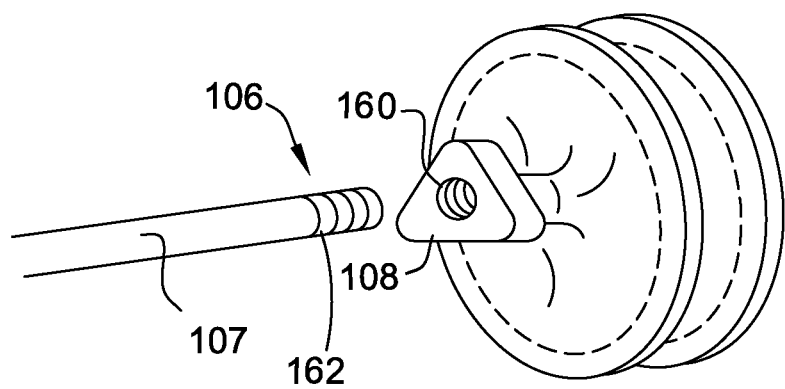
FIG. 9 illustrates one exemplary embodiment of delivery of the medical device to a target site, in accordance with the present disclosure.

When the placement of medical device 110 has been assessed and confirmed (e.g., by a physician), coupling member 106 of delivery device 102 is disconnected from connecting member 108 of medical device 110. As shown in FIG. 9, in some embodiments, connecting member 108 includes internal threads 160 configured to mate with external threads 162 of coupling member 106. In such cases, disconnecting coupling member 106 from connecting member 108 includes rotating delivery cable 107 in a rotational direction opposite to the direction of mated threads 160, 162. Thereafter, medical device 110 is considered fully deployed.

According to the present disclosure, medical device 110 is designed such that frame 112 can be recaptured and withdrawn or removed from medical device 110, after medical device 110 has been deployed at the target site. In at least some embodiments, device frame 112 cannot be recaptured for some period of time, or until a sufficient amount of endothelialization has occurred around biomaterial cover 114. The amount of time required for sufficient endothelialization to occur may depend on a number of factors, for example, the material used for biomaterial cover 114 or the target site at which medical device 110 is deployed. A physician may determine the appropriate time for removal of device frame 112. For instance, the physician may determine there is a medical reason for frame 112 to be removed (e.g., a need to intervene again in the same area to, for example, implant a mitral valve, conduct cardiac mapping, or implant an LAA occluder), and, after observing the amount of endothelialization that has taken place to confirm tissue ingrowth is sufficient to maintain occlusion of the target site, the physician may remove frame 112 at such a time. In at least some embodiments, the removal can occur after at least about 30-90 days after deployment and implantation of medical device 110.

To recapture and remove frame 112, an implanted medical device 110 (i.e., a medical device 110 that is currently in place at a target site) must be located. In some embodiments, confirmation may be made that a sufficient amount of endothelialization has taken place, specifically, that the amount of tissue ingrowth is sufficient to provide an occlusive effect.

Figure 7A:
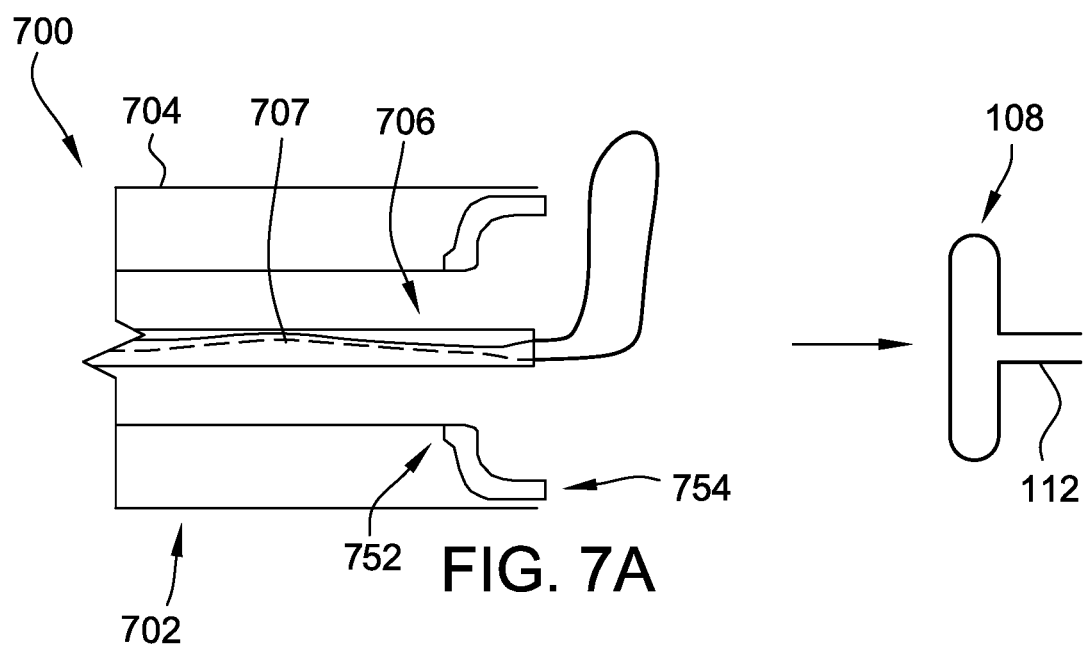
FIGS. 7A-7C illustrate one exemplary embodiment of recapture of the frame of the medical device in accordance with the present disclosure.
Figure 7B:
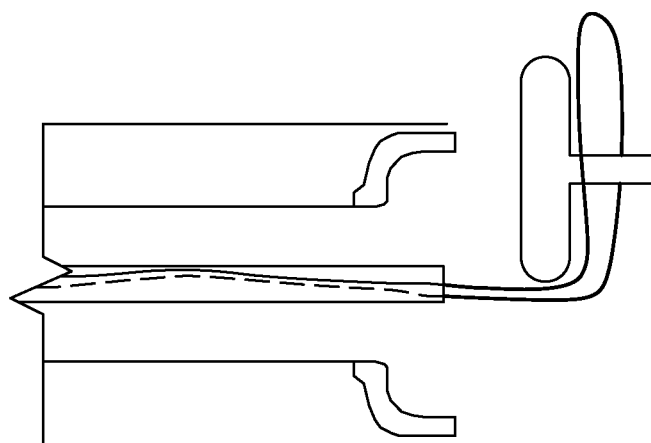
Figure 7C:
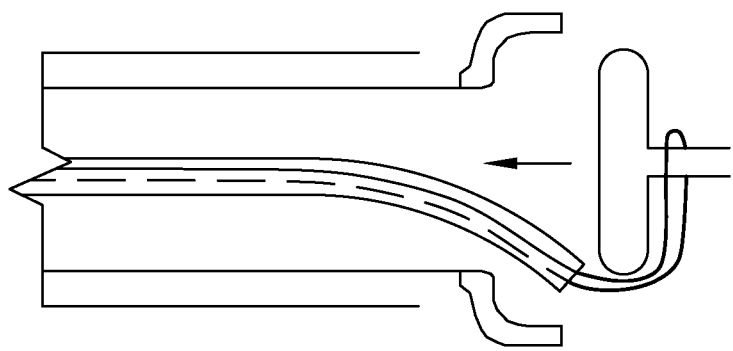
Figure 10A:
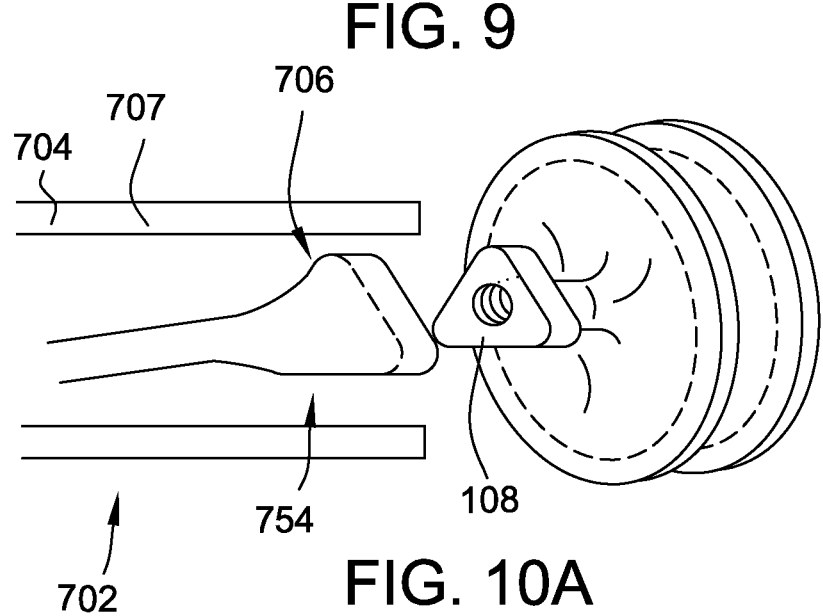
FIGS. 10A and 10B illustrate another exemplary embodiment of recapture of the frame of the medical device.
Figure 10B:
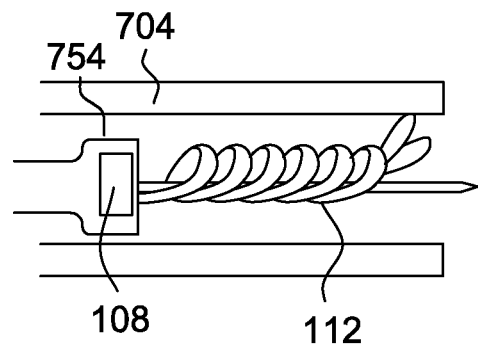

With reference to FIGS. 7A-7C as well as FIGS. 10A and 10B, in some embodiments, a recapture or retrieval system 700 is employed to recapture and withdraw or remove frame 112 from biomaterial cover 114 of the implanted medical device 110. In some instances, recapture system 700 includes one more elements in common with delivery system 100, such as delivery device 102 and/or delivery catheter 104. In other instances, recapture system 700 is wholly separate from delivery system 100. Accordingly, reference is made herein to a retrieval device 702 and a retrieval catheter (also referred to as a retrieval sheath) 704 of recapture system 700, regardless of their similarity with components of delivery system 100.

Recapture system 700 includes a recapture cable 707 that is advanced to the target site at which medical device 110 was previously deployed. Recapture cable 707 includes a coupling member 706 at the distal end thereof. Coupling member 706 is coupled to proximal end 120 of frame 112 (e.g., to connecting member 108). To retract prongs 126 from biomaterial cover 114, in some exemplary embodiments, frame 112 is rotated in a second direction 150 (see FIG. 4) opposite to first direction 128. This rotation, in second direction 150, causes prongs 126 of proximal and distal discs 116, 118 to be rotated opposite to their rotational shape and, therefore, rotated out of their original expanded shape, to retract or withdraw prongs 126 from pockets 144. Thereby, frame 112 is "de-coupled" from biomaterial cover 114.

Notably, in some embodiments, depending on the shape of frame 112 and/or prongs 126 (e.g., the thickness, stiffness, or shape of prongs 126), frame 112 does not need to be rotated to de-couple frame 112 from biomaterial cover 114. In such embodiments, frame 112 may be de-coupled from biomaterial cover 114 by applying only a proximally oriented force to frame 112.

As frame 112 is being or has been de-coupled from biomaterial cover 114, frame 112 can be withdrawn from biomaterial cover 114 and, therefore, medical device 110 at the target site, leaving only biomaterial cover 114 in place to provide the necessary occlusion of the target site.

In some embodiments, as shown in FIGS. 7A-7C, coupling member 706 is embodied as a loop or snare, which is advanced distally from retrieval catheter 704 towards connecting member 108 of frame 112 (see FIG. 7A). Coupling member 706 is attached to connecting member 108 by looping coupling member 706 around connecting member 108 (see FIG. 7B). Once coupling member 706 has been looped around connecting member 108, the snare is retracted into retrieval catheter 704 (see FIG. 7C) and/or retrieval catheter 704 is advanced distally until connecting member 108 is secured within retrieval catheter 704 or a docking cap 754. More specifically, a distal end 752 of retrieval sheath 704 and/or of recapture cable 707 is fitted with a docking cap 754 to secure connecting member 108 as frame 112 is withdrawn from biomaterial cover 114. Retrieval catheter 704 or docking cap 754 may be advanced into engagement with medical device 110 (e.g., proximal disc 116) to support biomaterial cover 114 while retracting frame 112 therefrom, to improve retention of biomaterial cover 114 within the target site during withdrawal of frame 112.

In one embodiment, as shown in greater detail in FIG. 10A, docking cap 754 and connecting member 108 have complementary shapes. For example, docking cap 754 has a non-circular shape that is complementary to a shape of connecting member 108, such that docking cap 754 is able to transfer rotational forces to connecting member 108. Although these complementary shapes are depicted as generally triangular in FIGS. 10A and 10B, it should be readily understood that various other regular and irregular non-circular shapes may be implemented (e.g., oval, rectangular, star-shaped, hexagonal, etc.). Additionally or alternatively, connecting member 108 may have a shape that is generally circular but that includes one or more indentations, extensions, and the like, such that the complementary shape of docking cap 754 may suitably impart rotational forces thereto. Once connecting member 108 has been secured within docking cap 754, connecting member 108 (and, thereby, frame 112) is rotated (via rotational forces from docking cap 154) in second direction 150 to de-couple and withdraw frame 112 from biomaterial cover 114, as described above. In some embodiments, as shown in FIG. 10B, this rotational force may cause frame 112 to twist upon itself into a reduced profile or configuration for retraction into retrieval catheter 704. In other embodiments, rotation of frame 112 de-couples frame 112 from biomaterial cover 114, and force applied by the distal end of retrieval catheter 704, as frame 112 is pulled proximally thereagainst, forces frame 112 into a reduced configuration for retraction of frame 112 into catheter 704.

In other embodiments, although not shown, a loop or snare may be coupled to connecting member 108, and coupling member 106 may engage the loop or snare. Moreover, in some embodiments, for example, where connecting member 108 has a small diameter, retrieval catheter 704 does not include a docking cap, and frame 112 is retracted fully into retrieval catheter 704 during withdrawal. In still other embodiments, coupling member 706 includes more than one hoop or snare that are deployed simultaneously to engage connecting member 108.

Figure 8:
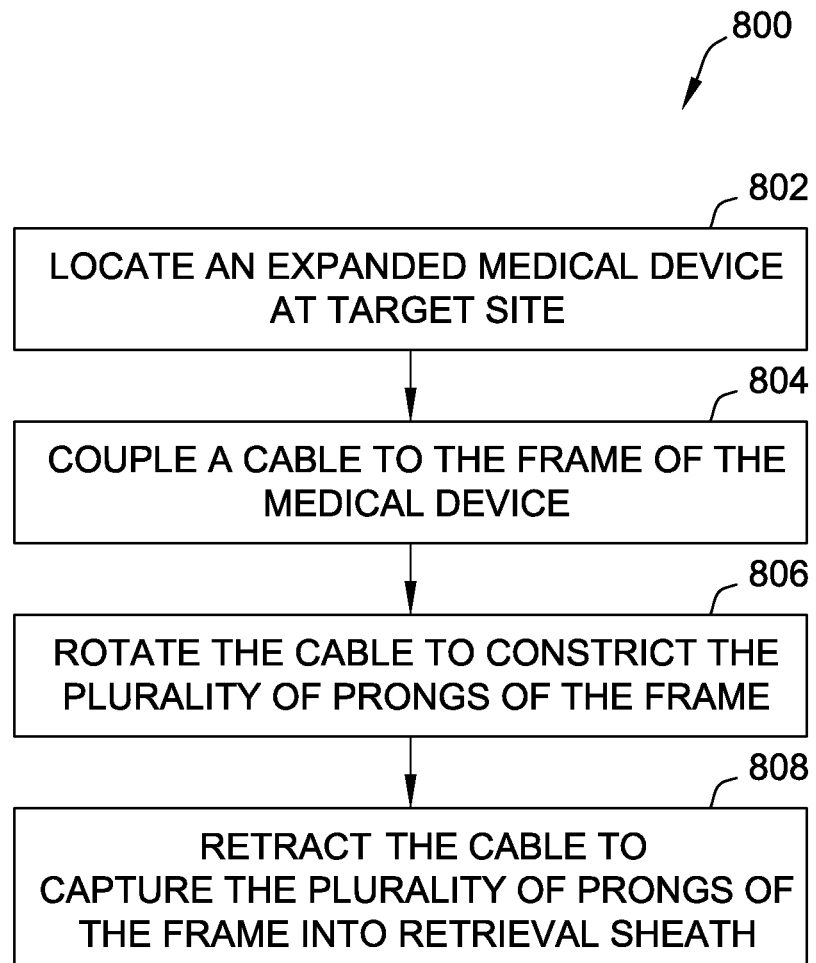
FIG. 8 is a flow diagram of a method of recapturing and removing a frame from a deployed medical device, in accordance with the present disclosure.

Turning now to FIG. 8 a flow diagram of a method 800 for recapturing a device frame from a medical device deployed at a target site in a subject is illustrated, according to one embodiment.

Method 800 includes locating 802 an expanded medical device (e.g., medical device 110, shown in FIG. 2) at the target site. As described herein, the medical device includes a frame having proximal and distal ends, the frame including a proximal disc at the distal end, a distal disc at the distal end, and a connecting segment having a proximal end and a distal end connecting the proximal and distal discs. Each of the proximal and distal discs includes a respective plurality of prongs, and each of the proximal and distal discs have a maximum cross-sectional dimension larger than the connecting segment. The medical device also includes at least one biomaterial cover, the biomaterial cover including an outer section and an inner section defining a cavity therebetween, wherein at least one of the proximal and distal discs of the frame is positioned in the cavity.

Method 800 also includes coupling 804 a cable (e.g., recapture cable 707, shown in FIG. 7A) to the frame of the medical device, rotating 806 the cable to constrict the plurality of prongs of the frame (e.g., to de-couple the frame from the at least one biomaterial cover), and retracting 808 the frame from the biomaterial cover of the medical device at the target site, to capture the plurality of prongs into the retrieval sheath.

Method 800 may include additional, alternative, and/or fewer steps, including those described herein. For example, in some embodiments, coupling 804 includes attaching a coupling member at a distal end of the cable to a connecting member at a proximal end of the frame. In some such embodiments, the attaching includes looping the coupling member around the connecting member (e.g., where the coupling member is embodied as a loop or snare). Moreover, in certain embodiments, method 800 does not include rotating 806 (e.g., in embodiments in which the frame does not need to be rotated to de-couple the frame from the biomaterial cover).

In some embodiments, each of the plurality of prongs are curved into a bent star configuration in which each prong of the plurality of prongs extends radially outwardly from the connecting segment and has a radius of curvature in a first direction defined between the connecting segment and a corresponding free end of the corresponding prong. In some such embodiments, rotating 806 includes rotating the cable in a second direction opposite to the first direction to de-couple the plurality of prongs from the at least one biomaterial cover.

While embodiments of the present disclosure have been described, it should be understood that various changes, adaptations and modifications may be made therein without departing from the spirit of the disclosure and the scope of the appended claims. Further, all directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. It is intended that all matter contained in the above description or shown in the accompanying drawings shall be interpreted as illustrative only and not limiting. Changes in detail or structure may be made without departing from the spirit of the disclosure as defined in the appended claims.

Many modifications and other embodiments of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific embodiments described and that modifications and other embodiments are intended to be included within the scope of the appended claims. Although specific terms are employed herein, they are used in a generic and descriptive sense only and not for purposes of limitation.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:
1. A medical device for treating a target site comprising:
a frame having proximal and distal ends, the frame comprising a proximal disc at the proximal end, a distal disc at the distal end, and a connecting segment connecting the proximal and distal discs, wherein each of the proximal and distal discs includes a respective plurality of prongs, the plurality of prongs each extending from the connecting segment to a free end; and at least one biomaterial cover, the at least one biomaterial cover comprising an outer section and an inner section defining a cavity therebetween, wherein at least one of the proximal and distal discs of the frame is positioned in the cavity, wherein the at least one biomaterial cover comprises a plurality of pockets corresponding to the plurality of prongs, and wherein the plurality of prongs are rotatable for withdrawal from the plurality of pockets.

2. The medical device of claim 1, wherein each prong of the plurality of prongs has a curvature extending radially outwardly from the connecting segment.

3. The medical device of claim 2, wherein the curvature is defined from the connecting segment to the free end of each of the plurality of prongs.

4. The medical device of claim 2, wherein the curvature extends in a generally counterclockwise direction.

5. The medical device of claim 4, wherein the prongs are rotatable in a generally clockwise direction opposite to the counterclockwise direction for withdrawal from the plurality of pockets.

6. The medical device of claim 1, wherein at least a portion of the plurality of prongs is retained within the at least one biomaterial cover during deployment of the medical device at the target site.

7. The medical device of claim 1, wherein each prong of the plurality of prongs has a curvature extending in a first direction and are rotatable in a second direction opposite the first direction.

8. The medical device of claim 1, wherein withdrawal of the plurality of prongs from the plurality of pockets enables de-coupling of the frame from the at least one biomaterial cover after deployment of the medical device at the target site.

9. The medical device of claim 8, wherein withdrawal of the plurality of prongs from the plurality of pockets enables withdrawal of the frame from the target site.

10. The medical device of claim 1, wherein the plurality of pockets are formed by one or more sutures.

11. The medical device of claim 10, wherein the one or more sutures extend through both the inner section and the outer section of the at least one biomaterial cover.

12. The medical device of claim 10, wherein the one or more sutures are sewn around a circumference of at least one of the inner section and the outer section of the at least one biomaterial cover.

13. The medical device of claim 10, wherein the one or more sutures comprise one or more bioabsorbable sutures.

14. The medical device of claim 10, wherein the at least one biomaterial cover is coupled to at least one of the proximal and distal discs by the one or more sutures.

15. The medical device of claim 1, wherein a proximal end of the connecting segment comprises a connecting member configured to couple the medical device to a retrieval device for retrieval of the medical device after deployment of the medical device at the target site.

16. The medical device of claim 1, wherein the frame comprises a shape-memory material.

17. The medical device of claim 1, wherein the at least one biomaterial cover surrounds at least a portion of the frame.

18. The medical device of claim 1, wherein the at least one biomaterial cover at least partially surrounds at least one of the proximal and distal discs.

19. The medical device of claim 1, wherein the inner section of the at least one biomaterial cover is removably coupled to the connecting segment of the frame.

20. The medical device of claim 1, wherein the at least one biomaterial cover is formed from a bioabsorbable polymer or from a tissue material.

\* \* \* \* \*